US012805745B2

(12) United States Patent
Kühn et al.

(10) Patent No.: US 12,805,745 B2
(45) Date of Patent: Nov. 24, 2026

(54) METHOD AND DEVICE FOR MONITORING AND/OR ADAPTING BREATH-HOLDING MAGNETIC RESONANCE EXAMINATIONS

(71) Applicant: Siemens Healthineers AG, Forchheim (DE)

(72) Inventors: Bernd Kühn, Uttenreuth (DE); Elisabeth Weiland, Erlangen (DE); Gregor Thörmer, Cadolzburg (DE); Silvia Bettina Arroyo Camejo, Fürth (DE); Julian Wohlers, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 19/010,469

(22) Filed: Jan. 6, 2025

(65) Prior Publication Data

US 2025/0228467 A1 Jul. 17, 2025

(30) Foreign Application Priority Data

Jan. 12, 2024 (DE) ..................... 10 2024 200 268.2

(51) Int. Cl.
*A61B 5/055* (2006.01)
*A61B 5/08* (2006.01)
*G01R 33/567* (2006.01)

(52) U.S. Cl.
CPC ............ *A61B 5/055* (2013.01); *A61B 5/0803* (2013.01); *G01R 33/5676* (2013.01)

(58) Field of Classification Search
CPC .... A61B 5/055; A61B 5/0803; G01R 33/5676
See application file for complete search history.

(56) References Cited

U.S. PATENT DOCUMENTS

| | | | | |
|---|---|---|---|---|
| 2013/0211236 | A1* | 8/2013 | Beck | A61B 5/7285 600/413 |
| 2015/0119696 | A1 | 4/2015 | De Oliveira | |
| 2017/0052239 | A1* | 2/2017 | Nagasawa | A61B 5/055 |
| 2017/0251949 | A1* | 9/2017 | Carinci | A61B 5/055 |
| 2018/0031665 | A1* | 2/2018 | Zeller | G01R 33/5676 |
| 2024/0407738 | A1* | 12/2024 | Alberts | G01R 33/567 |

FOREIGN PATENT DOCUMENTS

| | | | | |
|---|---|---|---|---|
| DE | 102013222103 A1 | | 5/2015 | |
| DE | 102016200954 A1 | | 7/2017 | |
| DE | 102016213632 A1 | | 2/2018 | |
| EP | 3438688 A1 | | 2/2019 | |
| KR | 20180048502 A | * | 5/2018 | A61B 5/055 |

OTHER PUBLICATIONS

The KR-20180048502 machine translation (Year: 2018).*

* cited by examiner

*Primary Examiner* — Alexei Bykhovski
(74) *Attorney, Agent, or Firm* — Lempia Summerfield Katz LLC

(57) ABSTRACT

A method, corresponding device, control device, and magnetic resonance tomography (MRT) system for monitoring and/or adapting breath-holding magnetic resonance (MR) examinations are disclosed. The method includes: acquiring a respiratory signal from a patient during a breath-holding MR scan; determining a respiratory behavior of the patient for the breath-holding MR scan from the respiratory signal; and outputting information about the respiratory behavior and/or outputting control commands based on the respiratory behavior.

15 Claims, 2 Drawing Sheets

METHOD AND DEVICE FOR MONITORING AND/OR ADAPTING BREATH-HOLDING MAGNETIC RESONANCE EXAMINATIONS

The present patent document claims the benefit of German Patent Application No. 10 2024 200 268.2, filed Jan. 12, 2024, which is hereby incorporated by reference in its entirety.

TECHNICAL FIELD

The disclosure relates to a method and a device for monitoring and/or adapting breath-holding magnetic resonance (MR) examinations, a control device for a magnetic resonance tomography (MRT) system, and an MRT system. In particular, the disclosure relates to automatic monitoring and adaptation of breath-holding MR examinations for the prevention of image artifacts.

BACKGROUND

In certain MR examinations, (e.g., an examination of the abdomen), it is important to prevent image artifacts caused by respiratory movement. For this reason, such scans are performed either synchronously with the respiratory movement (respiratory triggering) or the patient is asked to stop the respiratory movement for a short period (breath-holding MR examination). During this period, the tissue may not move and artifact-free images may be acquired.

In certain examples, breath-holding scans may be implemented over alternative scanning methods with respiratory triggering because the duration of scanning is shorter and such scans may produce better image quality.

The success of MR scans acquired while the breath is being held is influenced by how well the patient follows the respiratory commands and holds his or her breath for the duration of the MR scans. This depends individually on the abilities and situation of the patient. However, the scanning protocols which determine the duration of the scan may not be adapted to the individual patients, so that MR scans regularly have breathing-related artifacts and hence have to be repeated. A scanning protocol, or simply protocol for short, may include one or more pulse sequences. A pulse sequence may include a sequence of multiple RF pulses and/or gradient pulses.

This leads to a preventable prolongation of the duration of an examination and thus to increased costs. In addition, repetitions of breath-holding scans lead to further fatigue on the part of the patient and may further reduce the prospects of success of a scan with good image quality. The patient experience is also limited with each additional breath-holding scan, in particular those which exceed the time the individual may hold his or her breath.

For example, abdominal scans are currently performed either wholly manually or with the support of workflow software.

In the case of purely manual scans, a set of protocols exists for which the duration of scanning is predefined and is not adjusted to the patient's individual situation. If it is found during the examination that the duration of scanning is too long and image artifacts occur, these scans have to be repeated with protocols that have a shorter duration of scanning. This may be done by an operator, (for example, a medical technician or a physician), either adapting the protocols in the course of the examination or reverting to an alternative set of protocols.

If workflow support software is used, the operator defines a duration of scanning before the examination and thus the time for which the patient has to hold his or her breath. This value is based on an estimate of what duration is appropriate for the patient. Once this duration of scanning has been entered, the software automatically adapts all scanning protocols to this value. If this estimated breath-holding ability is not accurate, image artifacts may occur, and the duration of scanning has to be reduced with the help of the software.

In both cases, the duration of the entire examination is prolonged due to repetitions of scans.

SUMMARY AND DESCRIPTION

It is an object of the present disclosure to specify a method and a device for monitoring and/or adapting breath-holding MR examinations, a control device for an MRT system, and an MRT system, with all of which the above-described disadvantages are reduced.

The scope of the present disclosure is defined solely by the appended claims and is not affected to any degree by the statements within this summary. The present embodiments may obviate one or more of the drawbacks or limitations in the related art.

A method is used for monitoring and/or adapting breath-holding MR examinations. The method includes: acquiring a respiratory signal from a patient during a breath-holding MR scan; determining the respiratory behavior of the patient for this breath-holding MR scan from the respiratory signal; and outputting information about the respiratory behavior and/or outputting control commands based on the respiratory behavior, in particular to an operator. The information may be output via a display, in particular a monitor. The operator may be a person who performs the MR examination, in particular, operates the MRT system.

In order to reduce the number of examinations to be repeated, it is useful to monitor breathing and to adapt the duration of the individual scans to the patient's ability to hold his or her breath. The method monitors the respiratory behavior and may be used to control an MR scan automatically as a function of the respiratory behavior.

For the acquisition of the respiratory signal, use may be made of a system for physiological monitoring of the patient (PMU), which may be present on MR systems. Among other things, a PMU supplies signals for characterizing the patient's breathing, and may be used to perform breathing-triggered scans.

If the respiratory signal of the PMU is also acquired in connection with a breath-holding scan, a curve is obtained which shows a plateau in addition to the normal respiratory signals. This plateau is the respiratory signal while the breath is being held.

The respiratory signal, in particular the curve, provides information about the patient's respiratory behavior during the scan. These respiratory curves may be evaluated automatically in order to obtain information about how well a patient was able to follow the respiratory commands. This evaluation may be done either in real time or on conclusion of the respective scan.

When determining the patient's respiratory behavior for this breath-holding MR scan, it may be possible to determine the length in time of the plateau (i.e., the duration for which the breath is being held). Other possibilities may include the time as from which the breath was held or the gradient of the plateau or other parameters.

After this determination, the method may include outputting information about the respiratory behavior and/or outputting control commands based on the respiratory behavior. For this purpose, it may be of advantage to output such information only if the respiratory behavior was not optimal.

For example, the result of this determination or analysis may be that the patient was able to follow the respiratory commands sufficiently well so that no image artifacts are to be feared. In this case, no further action is necessary, and information does not necessarily have to be output. However, it may nevertheless be advantageous to output information to the effect that the respiratory behavior was good, for example a green logo or the note “respiratory behavior good.”

However, if it is found that the patient cannot follow the respiratory commands sufficiently well, (e.g., because the breath was not held for long enough or because the respiratory behavior exhibits a long delay compared to the respiratory commands, so that image artifacts are to be expected), information to this effect may be output to an operator or to a control system so the MR scan may be adapted manually or automatically.

Examples of cases of information outputs are listed below, which may represent an output individually or in combination.

The operator may be sent a message that the patient is not following the respiratory commands sufficiently and image artifacts may occur.

If the patient does not hold his or her breath for long enough, the operator may be recommended to adapt the scanning protocols or this adaptation is performed automatically, in order to prevent artifacts in the subsequent scans.

In the event of delays in implementing the respiratory commands, the start of the scan may be delayed accordingly in order to provide optimal synchronization of the breath-holding interval and the scan.

If the plateau of the respiratory curve has a strong gradient (positive or negative), the operator may be notified of this because this effect may lead to image artifacts.

If the patient’s ability to follow the respiratory commands is too greatly restricted, a switch to a different scan strategy may be recommended or performed. In certain examples, the different scan strategy may be a breathing-triggered scan or unsynchronized scan in free breathing.

One of the particular features of the disclosure or forms of embodiment thereof is that in breath-holding scans the breath-holding ability may be determined by evaluating a measurement, (e.g., the PMU signal), and no more estimates are needed. As a result, the duration of the breath-holding intervals may be adapted individually to the patient’s situation and there is no need to use a blanket duration of scanning, which is either too short for the patient and thus not effective or too long and may lead to image artifacts and scan repetitions.

In addition, the person is alerted at an early stage to possible problems and may make corresponding adaptations to the scanning protocols, in order to avoid further scans with an unsuitable breath-holding duration. These adaptations may be performed either manually or automatically. The latter is advantageous in order to shorten the examination process on the one hand and to establish uniform procedures on the other. Thanks to these automatic functions, inexperienced MRAs are in particular supported, and errors are prevented.

A device is used for monitoring and/or adapting breath-holding MR examinations. The device includes the following components: a PMU system configured to acquire a respiratory signal from a patient during a breath-holding MR scan; a determination unit configured to determine the patient’s respiratory behavior from the respiratory signal; and an output unit configured to output information about the respiratory behavior and/or to output control commands based on the respiratory behavior.

The function of the components of the device has already been described above. The device may be configured for the execution of the method as described herein.

A control device for an MRT system includes a device as disclosed herein. Alternatively, or additionally, the control device may be configured to perform a method in accordance with the disclosure.

An MRT system includes a control device as described herein.

The disclosure may be implemented in the form of a computer unit with suitable software. The computer unit may have one or more cooperating microprocessors or the like. In particular, it may be implemented in the computer unit in the form of suitable software program parts. A largely software-based implementation has the advantage that even computer units used previously may easily be upgraded using a software or firmware update to perform the methods disclosed herein. In this respect, the object is also achieved by a corresponding computer program product with a computer program which may be loaded directly into a memory device of a computer unit, with program sections to execute all acts of the method when the program is executed in the computer unit. In addition to the computer program, such a computer program product may include additional elements such as documentation and/or additional components, including hardware components such as hardware keys (dongles, etc.) for using the software.

For transport to the computer unit and/or for storage on or in the computer unit, use may be made of a computer-readable medium, (e.g., a memory stick, a hard disk or any other transportable or permanently installed data medium on which are stored the program sections of the computer program that may be read and executed by a computer unit).

Further particularly advantageous embodiments and developments of the disclosure emerge from the claims and the following description, wherein the claims in one claim category may also be developed analogously to the claims and parts of the description to form another claim category and in particular individual features of different exemplary embodiments or variants may also be combined to form new embodiments or variants.

In certain methods, a scanning protocol of an MR scan on this patient may be established based on the information about a patient’s respiratory behavior. This information about the respiratory behavior may in this case be derived directly or indirectly from information from the respiratory signal.

The information about the respiratory behavior may originate from a previous MR examination on the patient, for example, it may have been noticed during the last MR examination on the patient that the patient cannot hold his or her breath for very long. An MR scan may then be adapted directly to this circumstance.

In one embodiment of the method, the MR examination includes a plurality of MR scans. A scanning protocol of an MR scan may be established using the information about the respiratory behavior from one or more previous MR scans of the MR examination on the patient.

In certain examples, during an MR examination, not just a single scanning protocol is used, but multiple different scanning protocols are applied consecutively. In other words, a plurality of MR scans is performed. In one example, a pilot scan for the precise localization of an organ is performed, and a main scan or a successive scan of multiple contrasts is additionally performed.

In one embodiment of the method for determining the respiratory behavior, a respiratory curve may be created from the strength of the respiratory signal against time. To this end, the respiratory signal may be plotted against time. The respiratory behavior may then be determined from this respiratory curve. The respiratory curve may therefore be evaluated in order to obtain information about how well the patient was able to follow the respiratory commands. The time period in which the breath was held is represented in the curve as a characteristic curve with a rise at the beginning (inhalation), a plateau (progression while the breath is being held), and a fall at the end (exhalation). This respiratory curve may be evaluated by a mathematical calculation, for example, by determining the time and/or gradient of the rise, the length and/or gradient of the plateau and/or the time and/or gradient of the fall.

The determination of the respiratory behavior may include one or more of the following parameters: time of suspension of breathing; breath-holding duration (in other words the length in time of the plateau in the respiratory signal); gradient of a respiratory curve, in particular the gradient for the rise to the plateau or the gradient of the plateau; variations in multiple respiratory curves (in other words differences in the patient's behavior when holding his or her breath); or combinations thereof.

The respiratory behavior may be determined by comparison with a reference respiratory profile. This reference respiratory profile may be an idealized respiratory profile or an average respiratory profile of the patient. A comparison may be made so that the reference respiratory profile is present in the form of a respiratory curve and the patient's respiratory behavior is likewise present as a respiratory curve and both these respiratory curves are compared with one another. It is then in particular possible to find out whether the aforementioned parameters are being complied with or to what extent the reference respiratory profile differs from the patient's respiratory behavior.

In this case in particular value ranges may be specified, which establish whether or not a deviation is critical.

If the breath-holding duration lies below a predefined limit value, information may be output to the effect that the patient has not held his or her breath for long enough.

If the interval between the time of suspension of breathing after a corresponding command and the corresponding time of suspension of breathing of the reference respiratory profile is greater than a predefined limit value, information may be output to the effect that the patient has held his or her breath too late.

If a gradient of a respiratory curve lies outside a predefined value range, in particular the gradient of the plateau or the gradient of the rise, corresponding information may be output.

If variations in multiple respiratory curves of a patient lie outside a margin of variation, corresponding information may be output. This may be done by calculating a mean value and a standard deviation and by checking whether the standard deviation lies outside a value range.

In one embodiment of the method, one or more parameters of a person's respiratory command to the patient may be additionally acquired. In this connection, at least the time of the respiratory command, and a period of time between the time of the respiratory command and a reaction by the patient, in particular a time of suspension of breathing, may be determined in the respiratory signal following on from the respiratory command. Thus, the system looks at when exactly the patient reacted to the respiratory command.

If the period of time is longer than a predefined comparison period, information may be output to the effect that the patient followed the respiratory command too late. Thus, a scan may be cancelled manually or else not started at all. Alternatively, or additionally, the start of a subsequent MR scan on the patient may be delayed in accordance with the period of time. If the patient reacts too late to a respiratory command, this may be established by the respiratory signal. A scan may then only be started when a corresponding reaction by the patient (for example, an inhalation and holding of breath) occurs. This may again provide optimal synchronization of the breath-holding interval and the scan.

In one embodiment of the method, a gradient of the respiratory signal may be additionally determined during the breath-holding duration. If the absolute value of the gradient falls below a predefined limit value, in other words something changes in the patient's air balance during the presumed suspension of breathing, information to this effect is output and/or a scan is stopped. If the plateau is too steep, in other words if for example the patient breaths out slowly, or if any other movements took place, this may also lead to image artifacts.

If the breath-holding duration lies below a predefined limit value, scanning protocols of subsequent MR scans of the examination may be checked for their length in time. If the breath-holding duration lies below a predefined limit value, this means that the patient cannot hold his or her breath for long enough. In particular, if this is established for multiple breath-holding durations, it may be concluded that the patient's ability to hold his or her breath is restricted. The length in time of a scanning protocol, or the duration of scanning which this scanning protocol implies, may simply be determined by the scanning protocol itself.

If the length in time of a scanning protocol falls below the breath-holding duration, information in respect of the MR scan in question is output. Alternatively, the length in time of the MR scan in question may be adapted automatically when it has been concluded that the patient's ability to hold his or her breath is restricted. This may be done by shortening a scanning protocol or dividing a scanning protocol into multiple parts, which are then applied during different breath-holding phases. Thus, artifacts in the MR scans in question may be effectively prevented.

If it is established that a patient cannot follow the respiratory commands, or only poorly, in particular because the period of time between the time of the respiratory command and the time of suspension of breathing is too long or the breath-holding duration is too short, information in respect of a switch to another scan strategy may be output. Alternatively, another scan strategy may also be performed automatically, (e.g., a breathing-triggered MR scan or an unsynchronized MR scan in free breathing). This possibility is particularly advantageous for patients whose ability to hold their breath is extremely poorly developed.

Respiratory signals for multiple breath-holding MR scans on a patient may be acquired. The patient's respiratory behavior is then determined from the multiple respiratory signals. This has the advantage that statistical statements about the respiratory behavior may be made. In this case, a mean value, a maximum value, and/or a minimum value may be determined. In this connection, in particular a minimum value for a breath-holding duration is determined (to establish a limit value) and/or a maximum value for a period of time between the time of the respiratory command and the time of suspension of breathing (likewise to establish a limit value) and/or a mean value for a gradient is determined (to determine what is a normal gradient for the patient).

A device may include a protocol unit configured to adapt a scanning protocol for an MR scan based on the respiratory behavior from one or more previous MR scans.

The use of artificial intelligence (AI)-based methods for the method may be used. Artificial intelligence is based on the principle of machine-based learning and may be performed using an algorithm that is capable of learning and has been trained accordingly. The term "machine learning" may be used for machine-based learning, the principle of "deep learning" also being included here.

Components of the disclosure may be available as a "cloud service." Such a cloud service is used to process data, in particular by artificial intelligence, but may also be a service based on conventional algorithms or a service in which an evaluation by humans takes place in the background. A cloud service (also referred to below as "cloud" for short) may be an IT infrastructure in which storage space or computing power and/or application software may be made available via a network. The communication between the user and the cloud takes place by data interfaces and/or data transfer protocols. In the present case, the cloud service may provide both computing power and application software.

In connection with certain methods, a provision of data received in connection with the disclosure may take place via the network to the cloud service. This includes a computing system, which may not include the user's local computer. The method may be realized by a command constellation in a network. The data calculated in the cloud is later sent back to the user's local computer via the network.

BRIEF DESCRIPTION OF THE DRAWINGS

The disclosure is described in greater detail below with reference to the attached figures on the basis of various embodiments. The same components are provided with identical reference characters in the various figures. The figures may not be true to scale.

DETAILED DESCRIPTION

Figure 1:
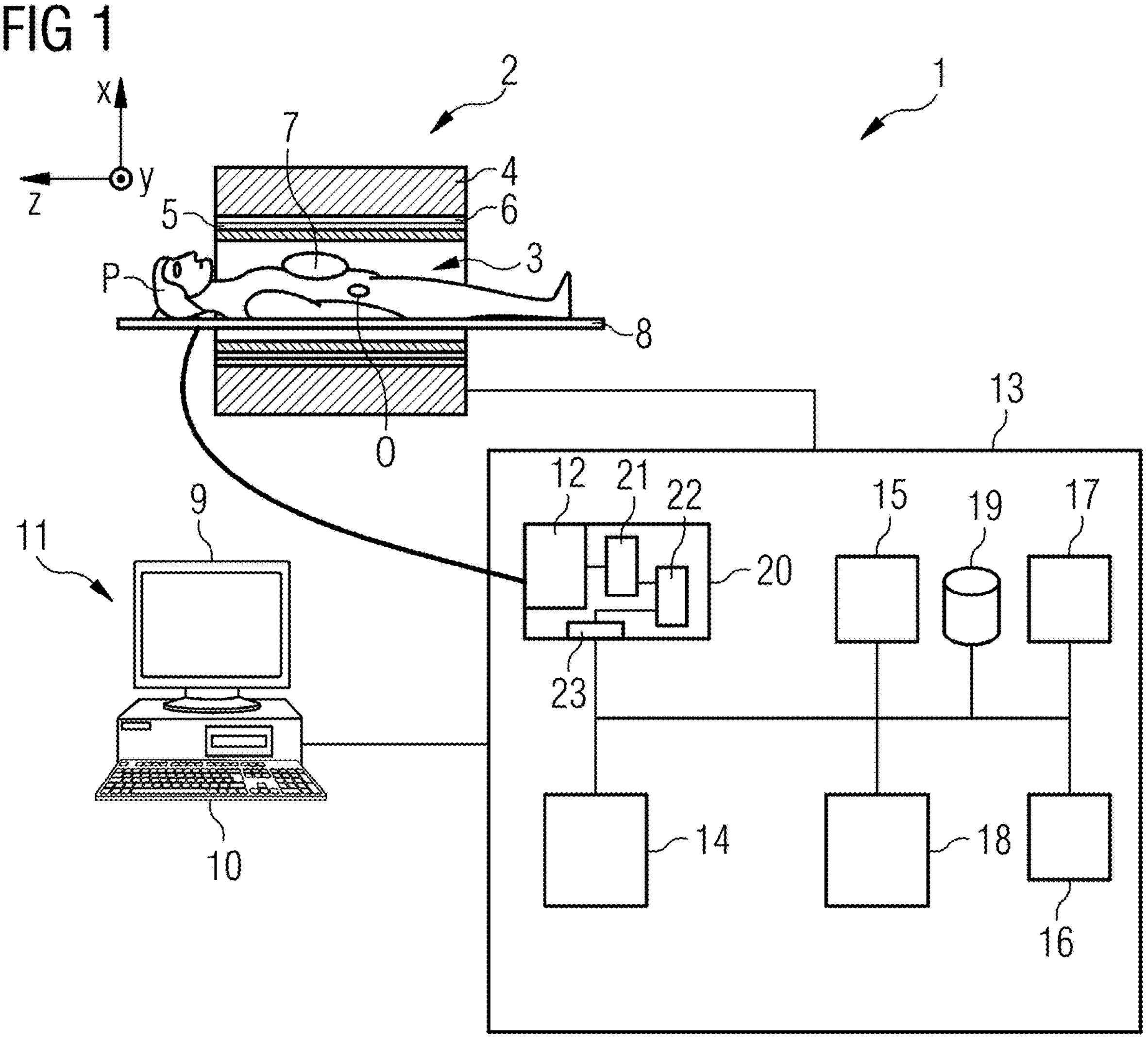
FIG. 1 is a schematic representation of a magnetic resonance tomography system in accordance with an embodiment.

FIG. 1 schematically shows a magnetic resonance tomography (MRT) system 1. The MRT system 1 includes the actual magnetic resonance scanner 2 with an examination space 3 or patient tunnel, into which a patient or test person in whose body the actual object under examination O is located is positioned on a couch 8.

The magnetic resonance scanner 2 may be equipped with a main field magnet system 4, a gradient system 6 (e.g., for generating gradient pulses), a radio frequency (RF) transmitting antenna system 5 (e.g., for transmitting RF pulses), and an RF receiving antenna system 7 (e.g., for receiving RF pulses). In the embodiment shown, the RF transmitting antenna system 5 is a whole-body coil permanently installed in the magnetic resonance scanner 2, whereas the RF receiving antenna system 7 includes local coils (symbolized here only by a single local coil) to be arranged on the patient or test person. In principle, however, the whole-body coil may also be used as an RF receiving antenna system and the local coils as an RF transmitting antenna system, providing these coils may each be switched to different operating modes. The main field magnet system 4 is here configured to generate a main magnetic field in the longitudinal direction of the patient, i.e., along the longitudinal axis of the magnetic resonance scanner 2 running in the z-direction. The gradient system 6 may include individually controllable gradient coils in order to be able to switch gradients in the x-, y- or z-direction independently of one another. Furthermore, the magnetic resonance scanner 2 (not shown) contains shim coils which may be designed in the normal way.

The magnetic resonance tomography system shown here is a whole-body system with a patient tunnel, into which a patient may be fully introduced. However, in principle, the disclosure may also be used on other magnetic resonance tomography systems, (e.g., with a C-shaped housing open at the side), wherein corresponding acquisitions of the object under examination O may be produced.

The magnetic resonance tomography system 1 further has a central control device 13 used to control the MR system 1. This central control device 13 includes a sequence control unit 14. This is used to control the sequence of radio-frequency pulses (RF pulses) and gradient pulses as a function of a selected pulse sequence or a sequence of multiple pulse sequences for acquiring multiple slices in a volume range of interest of the object under examination within a scan session. Such a pulse sequence may be predefined and parameterized within a scan protocol or control protocol. Different control protocols for different scans or scan sessions may be stored in a memory 19 and may be selected by an operator (and modified where appropriate) and then used to perform the scan.

By the selected pulse sequences or by the positioning of the above-mentioned RF receiving antenna system 7, the field of examination may be established.

To output the individual RF pulses of a pulse sequence, the central control device 13 has a radio frequency transmitting device 15 that generates and amplifies the RF pulses and feeds them into the RF transmitting system 5 via a suitable interface (not shown in detail). To control the gradient coils of the gradient system 6, in order to switch the gradient pulses appropriately in accordance with the predefined pulse sequence, the control device 13 has a gradient system interface 16. The diffusion gradient pulses and spoiler gradient pulses may be applied via this gradient system interface 16. The sequence control unit 14 communicates appropriately, for example by emitting sequence control data, with the radio frequency transmitting device 15 and the gradient system interface 16 to execute the pulse sequence.

The control device 13 additionally has a radio frequency receiving device 17 (likewise communicating appropriately with the sequence control unit 14), in order to receive magnetic resonance signals within the readout window predefined by the pulse sequence in a coordinated manner by the RF receiving antenna system 7 and thus to acquire the raw data.

A reconstruction unit 18 here takes over the acquired raw data and reconstructs magnetic resonance image data therefrom. This reconstruction may also take place on the basis of parameters, which may be predefined in the respective scan protocol or control protocol. This image data may then for example be stored in a memory 19.

How suitable raw data may be acquired in detail by irradiating RF pulses and switching gradient pulses and how MR images or parameter maps may be reconstructed therefrom is known in principle to the person skilled in the art and is therefore not explained in greater detail here.

The control device 13 further has a device 20 for monitoring and/or adapting breath-holding MR examinations on the MRT system 1. The device 20 includes a PMU system 12, a determination unit 21, and an output unit 22.

The PMU system 12 may be known and may be used in an MR system 1 for physiological monitoring of the patient P. The PMU system 12 supplies inter alia signals for characterizing the breathing of the patient P. A particular feature of the method is that the PMU system 12 is not (only) used for breathing-triggered scans but serves here primarily to acquire a respiratory signal from a patient P during a breath-holding MR scan.

The determination unit 21 serves to determine the respiratory behavior of the patient P from the respiratory signal. This is explained more fully in connection with the following figures.

The output unit 22 serves to output information about the respiratory behavior and/or to output control commands based on the respiratory behavior. This example relates to a system which independently writes messages or generates control commands and outputs them via a data interface 23.

The central control device 13 and, in certain examples, also the device 20 may be operated via a terminal 11 with an input unit 10 and a display unit 9, via which thus the entire MRT system 1 may be operated by one operator. Magnetic resonance tomography images may also be displayed on the display unit 9, and by the input unit 10, where appropriate in combination with the display unit 9, scans may be planned and started and in particular control protocols may be selected and where appropriate modified.

The MRT system 1 and the control device 13 may additionally have further components, not shown here individually but possibly present on such systems, (e.g., a network interface in order to connect the entire system to a network and to be able to exchange raw data and/or image data or parameter maps), as well as further data, (e.g., patient-related data or control protocols).

How suitable raw data may be acquired by irradiating RF pulses and generating gradient fields and how magnetic resonance tomography images may be reconstructed therefrom is known in principle to the person skilled in the art and is not explained in greater detail here.

Figure 2:
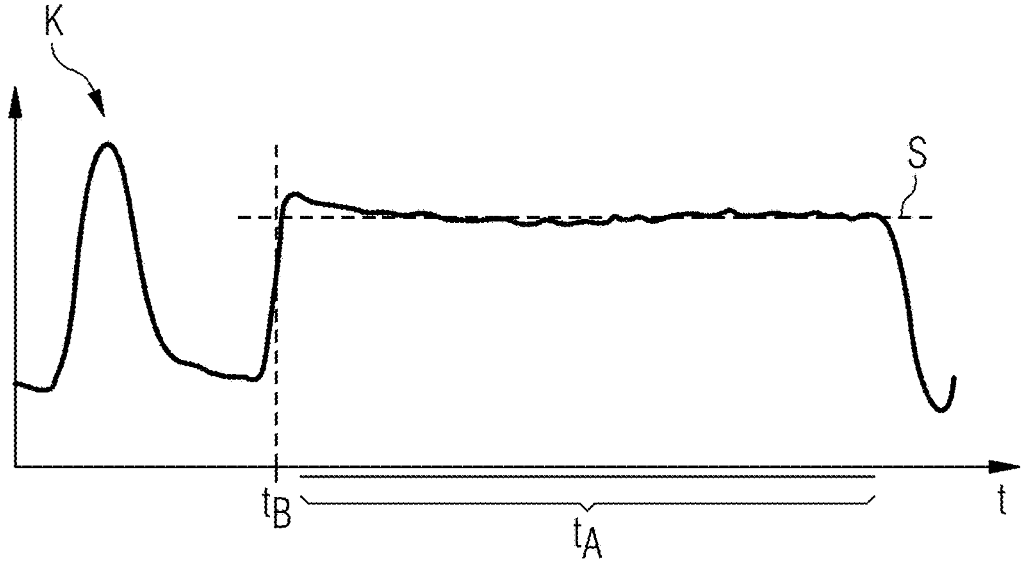
FIG. 2 depicts an example of a respiratory signal.

If the respiratory signal of the PMU system 12 is now also acquired during a breath-holding scan, a curve is obtained, as is shown in FIG. 2. Specifically, FIG. 2 shows an example of a respiratory signal during a breath-holding scan in the form of a respiratory curve K. The time t is plotted along the x-axis, the strength of the respiratory signal is plotted along the y-axis.

The respiratory curve K provides information about the respiratory behavior of the patient P during the scan. Thus, the example first shows a deep breath followed by an inhalation (rise), holding of breath (plateau), and exhalation (fall). This respiratory curve K may be evaluated to obtain information about how well the patient P was able to follow the respiratory commands of an operator, in particular a medical technician (see also FIG. 4). This evaluation may take place either in real time or on conclusion of the respective MR scan. Here, for example, the length in time of the plateau (the breath-holding duration $t_A$) may be determined. Other possibilities are for example the time of suspension $t_B$, as from which the breath was held, or the gradient S of the plateau. The result of this analysis may be that the patient P was able to follow the respiratory commands sufficiently well so that no image artifacts are to be feared. In this case, no further action is necessary. However, if it transpires that the patient P cannot follow the respiratory commands sufficiently well because, for example, he or she does not hold his or her breath for long enough or his or her respiratory behavior exhibits a strong delay compared to the respiratory commands, so that image artifacts are to be expected, various acts may follow.

The operator may be sent a message that the patient is not following the respiratory commands sufficiently well and image artifacts may occur.

If the patient does not hold his or her breath for long enough, a recommendation may be provided to the operator may to adapt the protocols, or the adaptation may be performed automatically, in order to prevent artifacts in the subsequent scans.

In the event of delays in implementing the respiratory commands, the start of the scan may be delayed accordingly, in order once again to provide optimal synchronization of the breath-holding interval and the scan.

If the plateau of the respiratory curve has a strong gradient (positive or negative), the operator may be notified of this, because this effect may lead to image artifacts.

If the patient's ability to follow the respiratory commands is restricted, the switch to another scan strategy may be recommended or performed. For example, alternatively to breath-holding scans, breathing-triggered scans or unsynchronized scans may be performed in free breathing.

Figure 3:
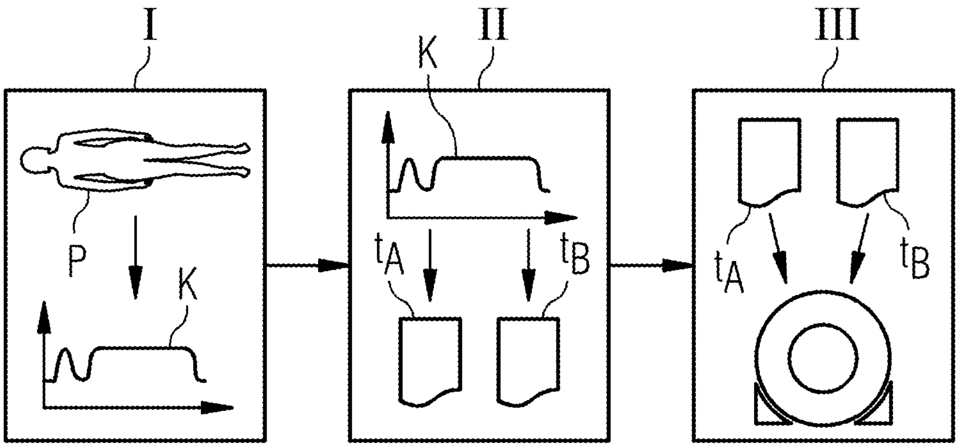
FIG. 3 depicts a flow chart of an example of operational sequence of a method.

FIG. 3 shows a flow chart for a possible operational sequence of a method for monitoring and/or adapting breath-holding MR examinations. As described above, this may be done by a PMU system 12 (see FIG. 1) and may be present in the form of a respiratory curve K as shown in FIG. 2.

In act I, a respiratory signal of a patient P is acquired during a breath-holding MR scan. For example, the breath-holding duration $t_A$ and the time of suspension $t_B$ is determined in the respiratory curve K.

In act II, the respiratory behavior of the patient P is determined for this breath-holding MR scan from the respiratory signal. For example, it is determined whether the breath-holding duration $t_A$ lies in a predetermined value range or does not fall below a predefined limit value and the time of suspension $t_B$ lies in a time to be expected.

In act III, information about the respiratory behavior and/or control commands based on the respiratory behavior are output. For example, the symbol of an MRT system here indicates that should problems occur in the respiratory behavior, scanning protocols are automatically adapted or the start of an MR scan is automatically adapted.

Figure 4:
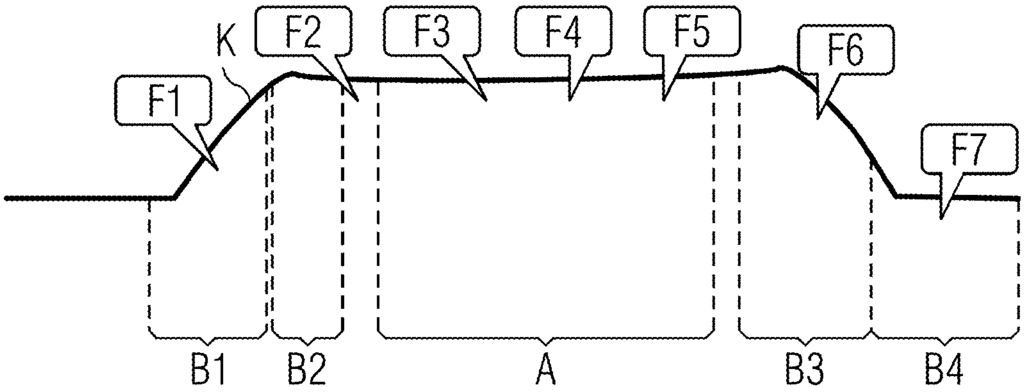
FIG. 4 depicts an example of a respiratory signal with respiratory commands.

FIG. 4 shows an example of a respiratory signal in the form of a respiratory curve K with respiratory commands B1, B2, B3, B4. First (from left to right), the respiratory command B1 "Inhale" is given, wherein a potential error F1 may be that this respiratory command B1 is followed too late. Then, the respiratory command B2 "Hold breath" is given, which is then followed by a data acquisition A after a short trigger time. Here, the potential errors F2, F3, F4, F5 may occur, if the trigger time is too short, the patient P did in fact breath, a gradient occurred in the plateau (for example due to slow exhalation) or the time of acquisition A is too long. Then follows the respiratory command B3 "Exhale", wherein a potential error F6 may be that this respiratory command B3 is followed too late. Finally, there is a pause, which may also be announced by a respiratory command B4. The potential error F7 may occur here if this pause is too long.

In conclusion, it is again noted that the disclosure described above in detail relates solely to embodiments that may be modified by the person skilled in the art in a variety of ways, without departing from the scope of the disclosure. Further, the use of the indefinite article "a" or "an" does not rule out that the features in question may also be present multiple times. Likewise, terms such as "unit" do not rule out that the components in question include multiple interacting subcomponents, which, where appropriate, may also be distributed spatially. The term "a number" is to be read as "at least one." Independent of the grammatical term usage, individuals with male, female or other gender identities are included within the term.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring and/or adapting breath-holding magnetic resonance (MR) examinations, the method comprising:

acquiring, by at least one processor of a MR system, a respiratory signal from a patient during a breath-holding MR scan;

determining, by the at least one processor, a respiratory behavior of the patient for the breath-holding MR scan from the respiratory signal, wherein the determining of the respiratory behavior comprises a determination of a starting time of suspension of breathing, a breath-holding duration, a gradient of a respiratory curve, variations in a case of multiple respiratory curves, or a combination thereof;

determining, by the at least one processor, a time of a respiratory command on the patient and a period of time between the time of the respiratory command and a reaction by the patient, wherein the reaction by the patient is the starting time of the suspension of breathing; and outputting, by the at least one processor, information with respect of a switch to a different scan strategy or automatically performing the different scan strategy when it is established that the patient cannot follow the respiratory command because the period of time between the time of the respiratory command and the time of suspension is longer than a first predefined length of time, or the breath-holding duration is shorter than a second predefined length of time.

2. The method of claim 1, further comprising:

establishing a scanning protocol of an MR scan based on the information about the respiratory behavior of the patient.

3. The method of claim 1, wherein the determining of the respiratory behavior comprises creating the respiratory curve from a strength of the respiratory signal against time and determining the respiratory behavior from the respiratory curve.

4. The method of claim 1, wherein, in an event that the breath-holding duration is below a predefined limit value, the information being output comprises that the patient has not held his or her breath for long enough.

5. The method of claim 1, wherein the multiple respiratory curves are compared with a reference respiratory profile.

6. The method of claim 1, wherein the information being output comprises the information with respect of the switch to the different scan strategy.

7. The method of claim 6, wherein the different scan strategy is a breathing-triggered MR scan or an unsynchronized MR scan in free breathing.

8. The method of claim 1, further comprising:

determining a gradient of the respiratory signal during the breath-holding duration; and outputting information or stopping the breath-holding MR scan when an absolute value of the gradient of the respiratory signal falls below a predefined limit value.

9. The method of claim 1, further comprising:

checking scanning protocols of subsequent MR scans of the examination for respective lengths in time when the breath-holding duration lies below a predefined limit value;

identifying a restriction of breathing of the patient when multiple breath-holding durations lie below the predefined limit value in the scanning protocols of the subsequent MR scans; and automatically shortening a length in time of a scanning protocol of an MR scan or dividing a scanning protocol into multiple parts following the identifying of the restriction of breathing of the patient.

10. The method of claim 1, wherein the different scan strategy is a breathing-triggered MR scan or an unsynchronized MR scan in free breathing.

11. The method of claim 1, wherein respiratory signals are acquired for multiple breath-holding MR scans on the patient including the breath-holding MR scan and the respiratory behavior of the patient is determined from the respiratory signals, and wherein a mean value, a maximum value, a minimum value, or a combination thereof is determined for a breath-holding duration and/or a maximum value for a period of time between the time of the respiratory command and the time of suspension and/or a mean value for a gradient.

12. A device for monitoring and/or adapting breath-holding magnetic resonance (MR) examinations, the device comprising:

at least one processor configured to:

acquire a respiratory signal from a patient during a breath-holding MR scan;

determine a respiratory behavior of the patient from the respiratory signal comprising a determination of a starting time of suspension of breathing, a breath-holding duration, a gradient of a respiratory curve, variations in a case of multiple respiratory curves, or a combination thereof;

determine a time of a respiratory command on the patient and a period of time between the time of the respiratory command and a reaction by the patient, wherein the reaction by the patient is the starting time of the suspension of breathing; and output information with respect of a switch to a different scan strategy or automatically performing the different scan strategy when it is established that the patient cannot follow the respiratory command because the period of time between the time of the respiratory command and the time of suspension is longer than a first predefined length of time, or the breath-holding duration is shorter than a second predefined length of time.

13. The device of claim 12, wherein the at least one processor is further configured to:

adapt a scanning protocol for an MR scan based on the respiratory behavior from one or more previous MR scans.

14. A magnetic resonance tomography (MRT) system comprising:

at least one processor configured to:

acquire a respiratory signal from a patient during a breath-holding magnetic resonance (MR) scan;

determine a respiratory behavior of the patient from the respiratory signal comprising a determination of a starting time of suspension of breathing, a breath-holding duration, a gradient of a respiratory curve, variations in a case of multiple respiratory curves, or a combination thereof;

determine a time of a respiratory command on the patient and a period of time between the time of the respiratory command and a reaction by the patient, wherein the reaction by the patient is the starting time of the suspension of breathing; and output information with respect of a switch to a different scan strategy or automatically performing the different scan strategy when it is established that the patient cannot follow the respiratory command because the period of time between the time of the respiratory command and the time of suspension is longer than a first predefined length of time, or the breath-holding duration is shorter than a second predefined length of time.

15. The method of claim 1, wherein the different scan strategy is automatically performed when the patient cannot follow the respiratory command or the breath-holding duration is too short.

* * * * *